United States Patent
Dolan

(10) Patent No.: US 8,815,160 B2
(45) Date of Patent: Aug. 26, 2014

(54) CHEMICAL VAPOR SENSOR WITH IMPROVED TEMPERATURE CHARACTERISTICS AND MANUFACTURING TECHNIQUE

(76) Inventor: Patrick Dolan, Seattle, WA (US)

(*) Notice: Subject to any disclaimer, the term of this patent is extended or adjusted under 35 U.S.C. 154(b) by 0 days.

(21) Appl. No.: 13/296,418

(22) Filed: Nov. 15, 2011

(65) Prior Publication Data

US 2012/0121467 A1    May 17, 2012

Related U.S. Application Data

(60) Provisional application No. 61/456,877, filed on Nov. 15, 2010.

(51) Int. Cl.
*G01N 15/06* (2006.01)
*G01N 33/00* (2006.01)
*G01N 33/48* (2006.01)

(52) U.S. Cl.
USPC ......... 422/83; 422/98; 422/82.02; 422/82.01; 436/43; 29/592; 29/592.1

(58) Field of Classification Search
USPC .............. 422/50, 68.1, 83, 98, 82.02, 82.01; 436/43; 29/592, 592.1
See application file for complete search history.

(56) References Cited

U.S. PATENT DOCUMENTS

| | | | |
|---|---|---|---|
| 2,294,148 A | 8/1942 | Kline et al. | |
| 2,777,957 A | 1/1957 | Walkup | |
| 2,825,814 A | 3/1958 | Walkup | |
| 2,836,725 A | 5/1958 | Vyverberg | |
| 2,919,848 A | 1/1960 | Howe | |
| 2,934,649 A | 4/1960 | Walkup | |
| 2,937,943 A | 5/1960 | Walkup | |
| 2,982,647 A | 5/1961 | Carlson et al. | |
| 3,001,849 A | 9/1961 | Walkup | |
| 3,013,901 A | 12/1961 | Bugosh | |
| 3,023,731 A | 3/1962 | Schwertz | |
| 3,045,198 A | 7/1962 | Dolan et al. | |
| 3,113,179 A | 12/1963 | Glenn, Jr. | |
| 3,196,011 A | 7/1965 | Gundlach et al. | |
| 3,307,941 A | 3/1967 | Gundlach | |
| 4,224,595 A | 9/1980 | Dolan | |
| 4,752,761 A | 6/1988 | Dolan | |
| 5,009,708 A | 4/1991 | Grunwald et al. | |
| 6,012,327 A | 1/2000 | Seth et al. | |
| 6,216,545 B1 * | 4/2001 | Taylor | 73/862.046 |
| 6,433,694 B1 | 8/2002 | Dolan | |
| 6,454,923 B1 * | 9/2002 | Dodgson et al. | 204/415 |
| 7,059,203 B2 * | 6/2006 | Asai et al. | 73/862.046 |

(Continued)

OTHER PUBLICATIONS

Nakade, M.; Ogawa, M. "Synthesis and characterization of zinc oxide fine particles coated with titania/PDMS hybrid," J. Mater. Sci., 2007, vol. 42, pp. 4254-4259.

(Continued)

*Primary Examiner* — Brian J Sines
(74) *Attorney, Agent, or Firm* — FSP LLC

(57) ABSTRACT

A vapor sensor is constructed from a single glass filament less than 2 millimeters in diameter and greater than 1 millimeters in length, the filament having a first end and a second end separated by a long axis and comprising electrodes at each end, coated with a resilient material, and a first layer of conducting particles embedded in the resilient material and forming a conducting path between ends of the filament.

20 Claims, 7 Drawing Sheets

2 resilient stratum
4 non-conducting filament substratum
6 conducting particles

(56) References Cited

U.S. PATENT DOCUMENTS

| | | |
|---|---|---|
| 7,186,381 B2 | 3/2007 | Penner et al. |
| 2010/0215547 A1 | 8/2010 | Dolan |
| 2011/0200487 A1* | 8/2011 | Dolan .......................... 422/90 |

OTHER PUBLICATIONS

Oyabu, T.; Osawa, T.; Kurobe, T. "Sensing characteristics of tin oxide thick film gas sensor," J. Appl. Phys. vol. 53 (11), 1982, pp. 7125-7130.

* cited by examiner

CHEMICAL VAPOR SENSOR WITH IMPROVED TEMPERATURE CHARACTERISTICS AND MANUFACTURING TECHNIQUE

PRIORITY CLAIM

This application claims priority under 35 U.S.C. 119 to U.S. application No. 61/456,877 filed on Nov. 15, 2010, which is incorporated herein by reference in its entirety.

BACKGROUND

Conventional vapor sensors exhibit significant response when subjected to temperatures above 30 C. This temperature response is of a magnitude that can be confused with the response caused by exposure to low concentrations of chemical vapor, for example gasoline vapor in the neighborhood of its lower flammability limit (LFL) of 1.4%

BRIEF DESCRIPTION OF THE DRAWINGS

In the drawings, the same reference numbers and acronyms identify elements or acts with the same or similar functionality for ease of understanding and convenience. To easily identify the discussion of any particular element or act, the most significant digit or digits in a reference number refer to the figure number in which that element is first introduced.

DETAILED DESCRIPTION

Preliminaries

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other.

Herein, "approximately" or "substantially" as applied to ranges means that more than half of the described elements fall within the range, although of course in any composition some (e.g. a low percentage, for example but not exclusively less than 10%-20%) of the elements may fall outside the range due to inherent limitations in design precision, manufacturing, filtering, separation, etc. The amounts that one skilled in the art would understand to "approximately" or "substantially" fall within or outside a range may depend upon the precision of the materials employed, the cost, the source of the materials, the manufacturing process, and possibly other factors. "Approximately" or "substantially" as applied to a particular value, unless otherwise specified, means falling within 20% of the particular value.

Overview

A vapor sensor comprises a resilient sub-stratum that anchors embedded conductive particles, applied to a non-resilient base formed from a non-conducting filament whose diameter is on the order of the size of the conductive particles. The filament forms the non-resilient base of the sensor. The filament's diameter less is than 2 millimeters, and typically 0.1 millimeters or less. The filament length is more than 1.0 millimeter, but typically 5 millimeters or more. The sensor exhibits reduced sensitivity to temperature while maintaining a high sensitivity to chemical vapor. In general, the particles each have a radius that is greater than a tenth and less than twice a radius of the filament.

Description of Particular Embodiments

Figure 1:
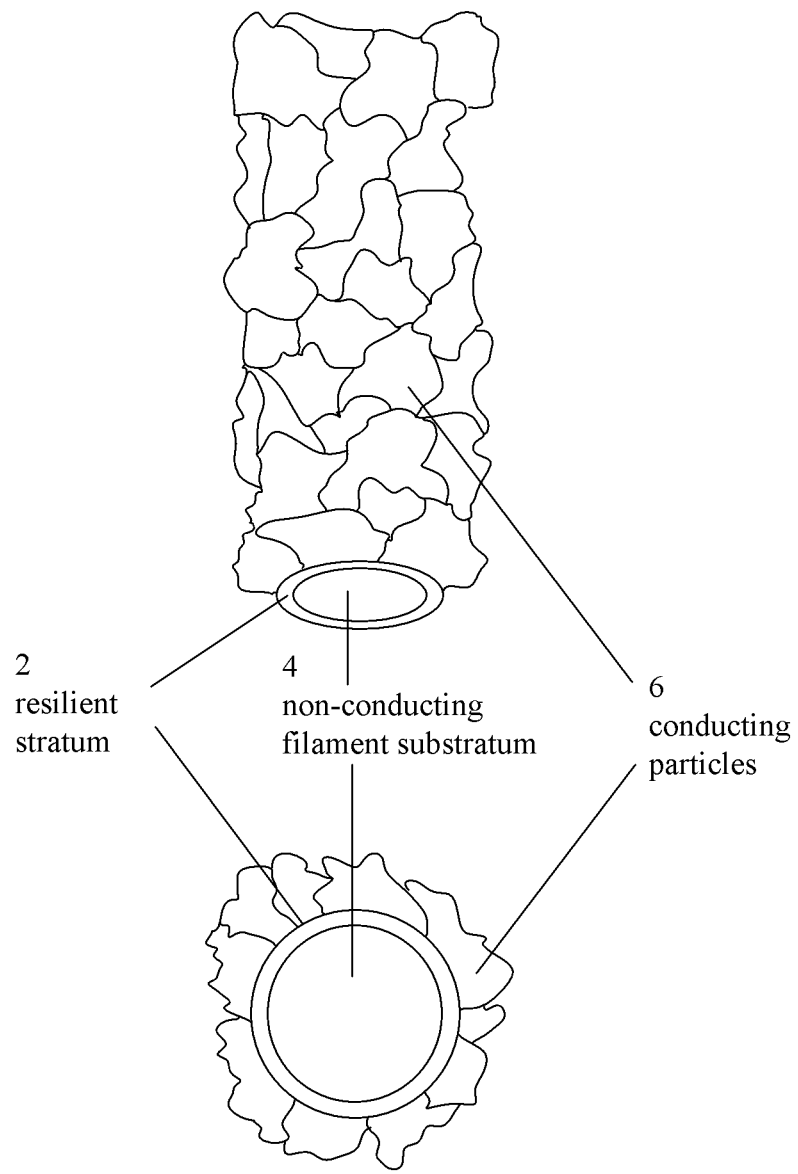
FIG. 1 illustrates a first embodiment of a vapor sensor implemented using a fiber.

FIG. 1 illustrates vapor sensor implemented using a fiber. The sensor comprises a resilient stratum 2, a non-conducting filament substratum 4, and a layer of conducting particles 6. The conducting particles 6 are chemically bonded to the resilient stratum 2.

As a radius of the filament 4 is decreased, the temperature sensitivity of the sensor is decreased. The sensitivity of the overall sensor to organic vapor also decreases with decreasing radius of the filament 4, but to a lesser extent than the decrease in temperature sensitivity. The net result for certain ranges of radii of the filament is a temperature insensitive sensor that produces a useful electrical response to organic vapor. For example, one embodiment is constructed from an optical (e.g., glass) filament having an approximately 800 micron radii, coated with particles of palladium. TABLE 1 shows electrical resistance for different radii (top row) of this first embodiment sensor at different temperatures (left column, Celsius). Another embodiment of a sensor is constructed from a 50 micron optical fiber coated with graphite particles. TABLE 2 shows electrical resistance for different radii (top row) of this second embodiment sensor at different temperatures (left column, Celsius).

TABLE 1

|    | 1.75 mm | .110 mm | .065 mm | .035 mm |
|----|---------|---------|---------|---------|
| 20 | 36      | 43      | 48      | 53      |
| 25 |         |         |         |         |
| 30 | 6160    | 53      | 50      | 53      |
| 35 |         |         |         |         |
| 40 | 1000000 | 77      | 55      | 57      |
| 45 |         |         |         |         |
| 50 |         | 220     | 103     | 61      |
| 55 |         |         |         |         |
| 60 |         | 3000    | 451     | 75      |

TABLE 2

|    | 1.75 mm | .11 mm | .035 mm |
|----|---------|--------|---------|
| 20 | 2021    | 4206   | 19800   |
| 25 |         |        |         |
| 30 | 6160    | 4998   | 20510   |
| 35 |         |        |         |
| 40 | 22150   | 16588  | 21570   |
| 45 |         |        |         |
| 50 | 156900  | 47100  | 23290   |
| 55 |         |        |         |
| 60 | 5830000 | 129900 | 26050   |

The sensor changes electrical resistance in response to changing organic vapor concentrations. Any electrical circuit device/circuit that can measure resistance may be used to monitor the condition of the fiber sensor. Such devices are known by those having skill in the art.

One embodiment of a sensor comprises an approximately 100 micron diameter filament with less than 500 micron diameter particles of flake graphite deposited thereupon.

Figure 2:
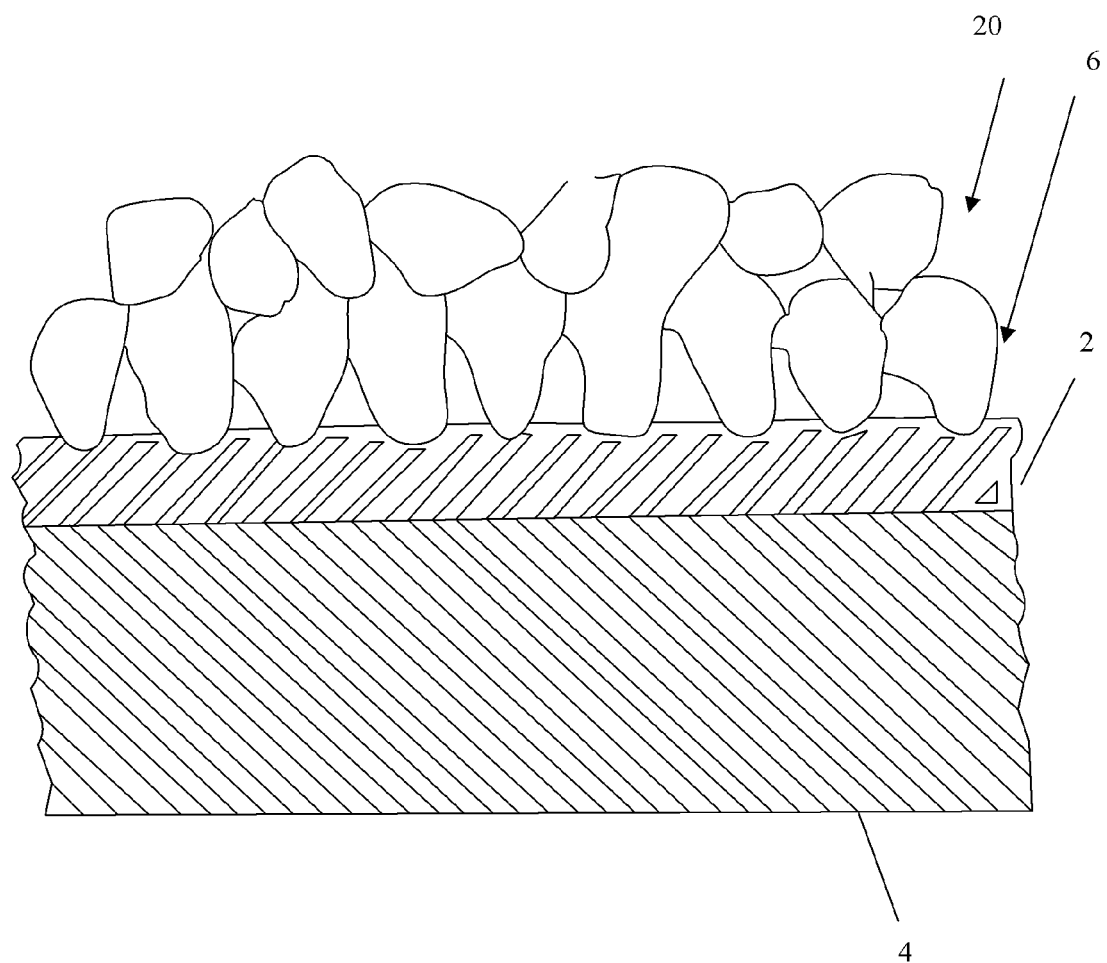
FIG. 2 illustrates a second embodiment of a vapor sensor implemented using a fiber.

FIG. 2 illustrates a second embodiment of a fiber vapor sensor. This embodiment comprises a layer of conducting particles 6 chemically bonded to the resilient stratum 2, and a second layer of particles 20 attached to the layer of conducting particles 6 through particle-to-particle attractive forces which are not chemical bonds, but which are, for example Van Der Waal forces.

A first portion of the conductive particle layer 6 is electrically coupled with a first conductive lead. A second conductive lead is electrically coupled with a second portion of the conductive layer 6, forming an electrical circuit with a measurable resistance.

A sensor such as described in FIG. 1 or 2 may rapidly determine changes in an environment from one containing a relatively low, or no, concentration of flammable gasoline vapor and/or household solvents, to one containing a gasoline or other vapor concentration above 50% of a pre-established lower flammability limit (e.g., 0.7% for gasoline vapor).

The resilient stratum 2 may comprise an elastomeric material composed essentially of 100% silicone, for example. The conductive particles 6 may comprise palladium particles generally adhered to and at least partially covering the stratum 2. If palladium particles are used, they may generally be less than or equal to 0.55 microns in diameter on average.

The sensor comprises electrically conductive absorbent particles 6 resiliently embedded in the stratum 2 and forming an electrical conductive path. The stratum 2 may comprise a siloxane having the formula R2SiO, where R is an alkyl group. The siloxane may be, for example, methoxypolydimethylsiloxane. The stratum may be, for example 100% silicone. Each particle 6 may be independently anchored to the stratum 2. The resistance of the electronically conducting path varies in response to the presence of an adsorbent medium exposed to the particles.

The adsorbent particles 6 of a first size are attached to the stratum 2, extending outwardly from the stratum 2 in a position to be exposed to the adsorbate medium, and having a resilient anchoring force against movement beyond a particular magnitude. In one embodiment the particles 6 have an average and/or median size less than 500 microns in diameter.

An additional layer of electrically conducting particles 20 may be attached (e.g., FIG. 2) by particle-particle cohesive forces to the particles 6. The particles 20 may be on or around the same average size as particles 6 and interspersed on top of and superior to the particles 6. The particles 20 may be attached to the particles 6 only by particle-particle cohesive forces, not chemical bonding. They have an anchoring force against movement of magnitudes different than the first higher magnitude. The particles 6 and particles 20 engage one another externally of the surface to form the electrical conducting path. Absorption forces cause the adsorbate to force the particles 6 and 20 apart and thus substantially change the resistance of the conductive path. Substantial changes in resistance may not be caused by increases in temperature near 125 F.

Particle-particle cohesion may be caused by Van Der Waal's attractive forces between the particles 6 and 20. The particles 6 and 20 may be palladium. The particles 6 comprising the first layer need not be the same size or material as the particles 20 of the second layer. For instance, the particles 6 may be comprised of silver particles while the particles 20 may be comprised of palladium particles. The particles 6 and 20 may be composed of one or more members of the group one of palladium, graphite, tungsten disulfide, silver, platinum, aluminum, gold, ruthenium, tantalum, iridium, or carbon.

The stratum 2 is attached to a fiber 4. The stratum 2 may be a flowable self-leveling silicone and the particles 6 may be comprised of palladium particles of diameters between 0.25 microns and 0.55 microns. The particles form a conductive path. When the sensor is exposed to gasoline or other organic vapor, molecules of the vapor adsorb to the surface of the particles to form an electrically insulating layer between each particle.

Because the particles 6 and/or 20 are not enclosed by the stratum 2, further cross-linking of the stratum does not cause sensor aging to the same extent in the layer of particles 6. The second layer of particles 20 has no contact with the stratum 20 and therefore is almost completely unaffected by any additional cross-linking of the resilient layer.

Limiting particles 6 and/or 20 to a diameter of less than 5 microns may substantially reduce sensitivity to increasing temperature while maintaining sensitivity to gasoline or other organic vapor.

In one embodiment, the sensor comprises a 100 micron diameter filament with ruthenium particles less than 100 microns in diameter, beneath a top layer of tungsten disulfide particles less than 10 microns in diameter.

Figure 3:
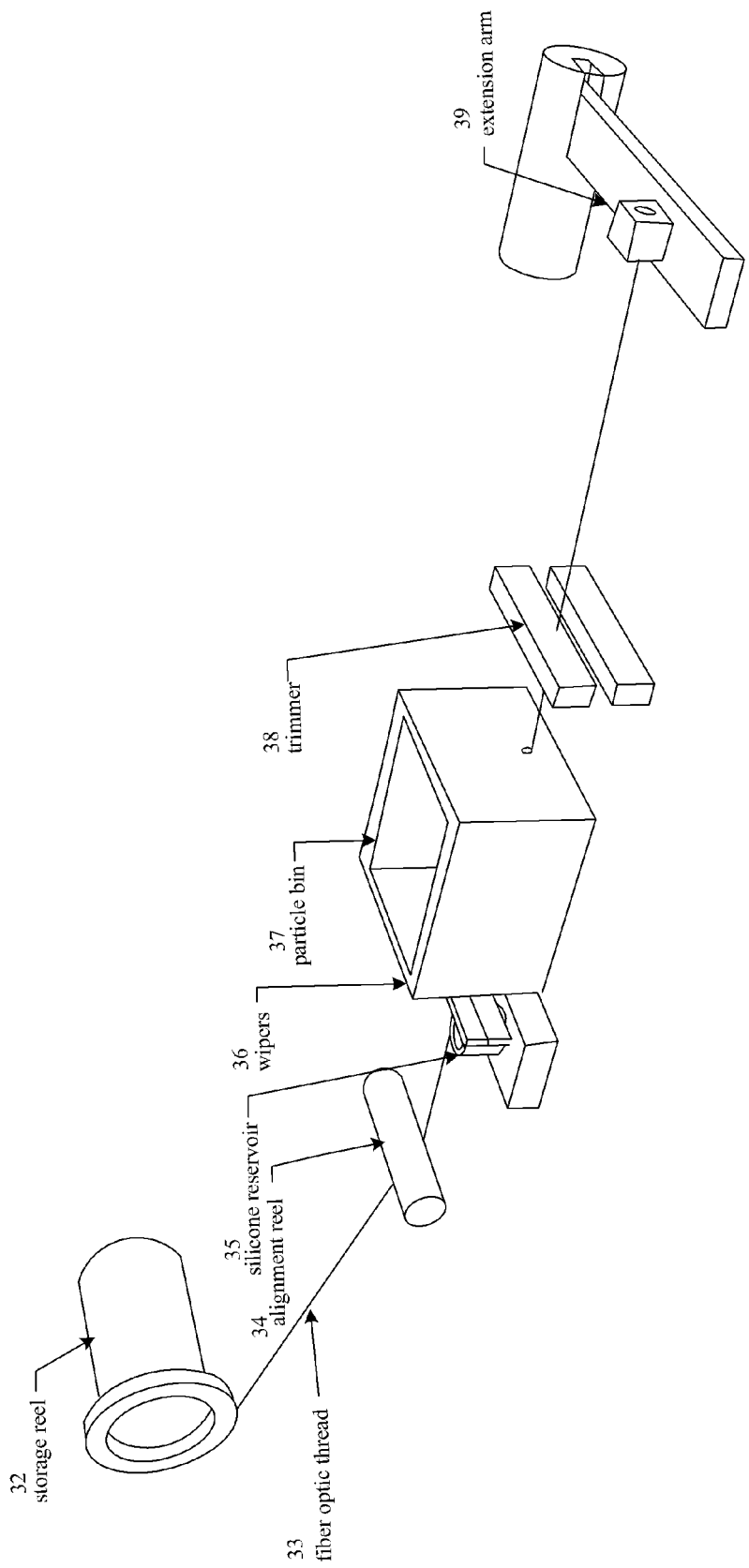
FIG. 3 illustrates the manufacture of a fiber vapor sensor.

FIG. 3 shows a manufacturing apparatus for creating an optical fiber based vapor sensor. Fiber 33 is drawn from a storage reel 32 across alignment rail 34 and through silicon applicator 35. This produces a fiber with a non-conducting filament substratum and a resilient stratum. Wipers 36 remove excess silicon before the fiber is drawn through a particle bin 37. The conducting particles are deposited onto the resilient stratum. A trimmer 38 cuts the fiber into useful lengths. An extension arm 39 is used to pull a length of fiber (e.g., 18-24 inches) through the silicone applicator 35, wipers 36, and particle bin 37. Additional layers of particles (non-chemically bonded, e.g. as illustrated in FIG. 2) may be deposited after curing.

This manufacturing technique is conducive to fabricating long continuous lengths of sensor filament that can be cut into smaller sections. This results in substantially lower manufacturing costs and production time on a sensor by sensor basis. Spools of filament can be drawn through wipers containing uncured resilient strata material, then immediately drawn through bins containing the electrically conducting particles to provide long lengths of completed sensor filament. The completed sensor filament, thus made, can then be drawn through a bin containing tungsten disulfide, if desired, for additional temperature stability. These long lengths of completed sensor filament can be subsequently chopped into quantities of shorter sensor segments.

Figure 4:
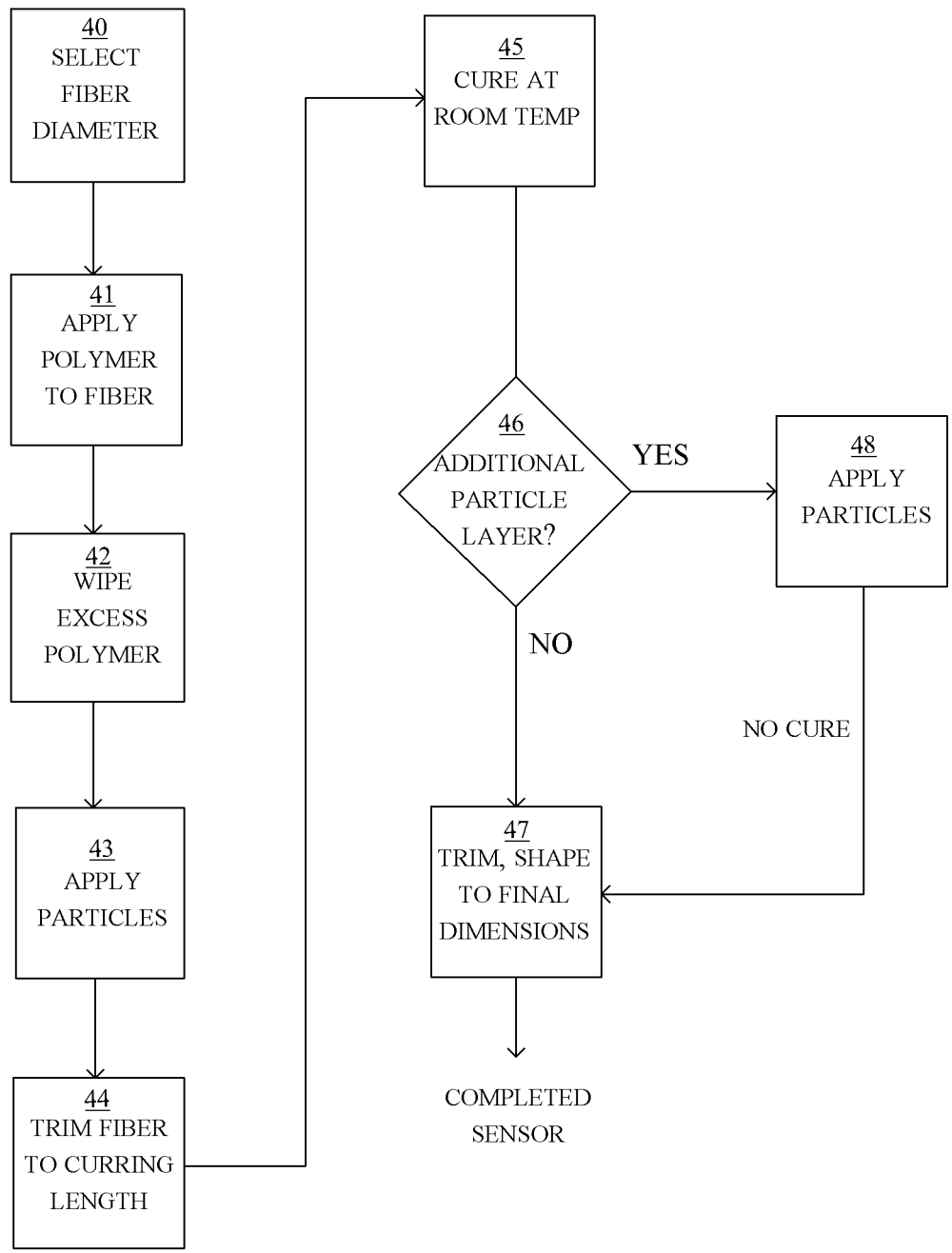
FIG. 4 is a flow chart showing a process of manufacturing a fiber vapor sensor.

FIG. 4 illustrates a process of manufacturing an optical fiber based vapor sensor. A fiber diameter is selected 40 and a polymer coating is applied to the fiber 41, such as silicone, natural and synthetic rubbers, fluro-silicones, adhesives such as 3M Fast Cure 5200, polyethylene adhesives, acrylic adhesives, or other resilient elastomers. Excess polymer is wiped 42 from the fiber and a layer of conductive particles is applied 43. The fiber is trimmed to a curing length 44 and cured at ambient temperature 45. Note the curing may occur at other temperatures to slow or accelerate the process. An additional particle layer may be applied 46. If an additional particle layer is applied, it is not chemically bonded to the first particle layer 48. No curing is necessary after applying the second layer particles, because they are not chemically bonded to the first particle layer. The fiber is trimmed and shaped to its final dimensions 47.

Figure 5:
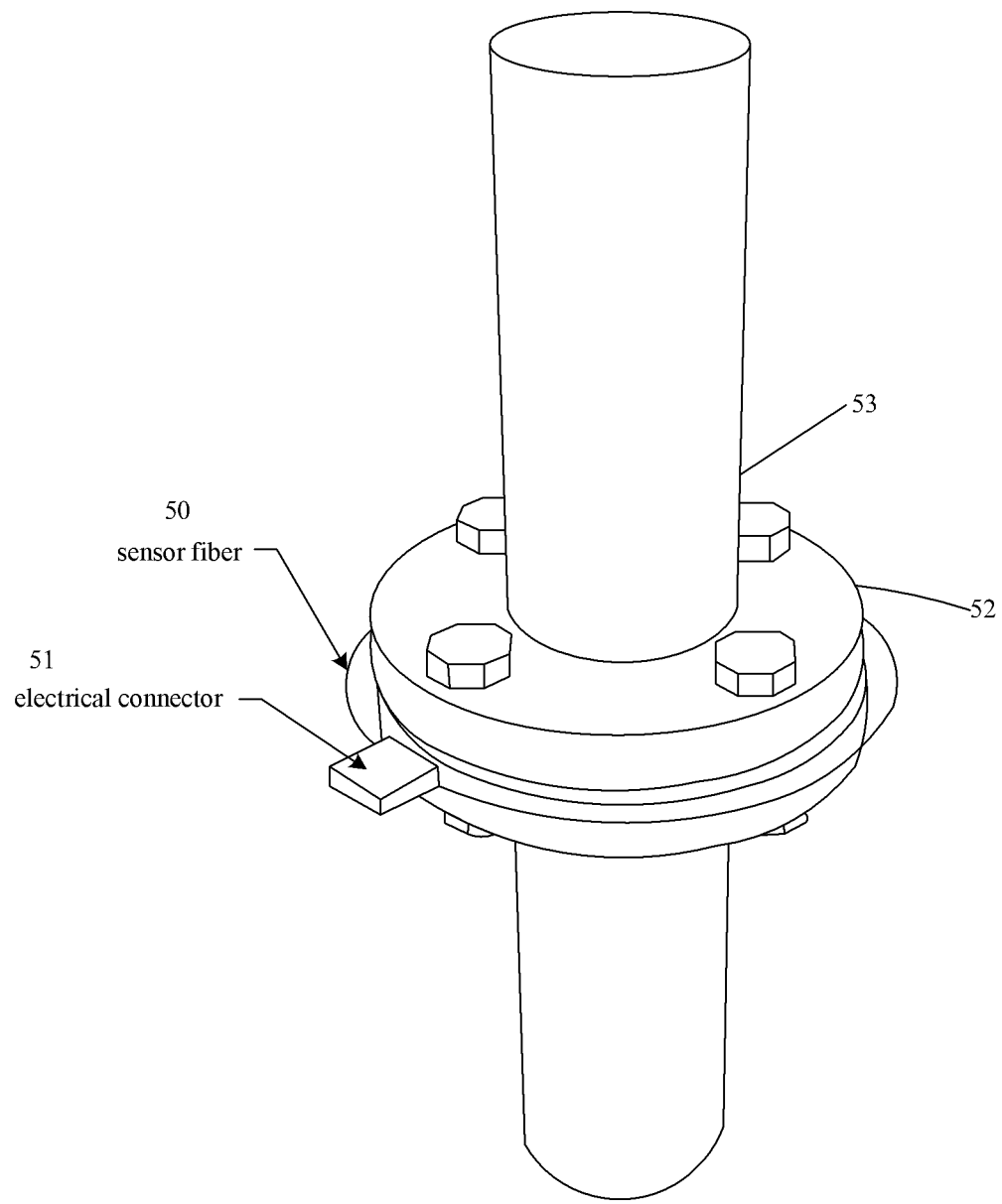
FIG. 5 illustrates a valve utilizing a fiber vapor sensor.

FIG. 5 shows the application of sensor fiber to detecting gas leaks around or near a flange. Examples of gases that may be detected are propane and natural gas. A gas pipe 53 is joined to another section of pipe by using a flange 52 such as an ASME flange. A sensor fiber 50 encircles the flange 52 where the two pipe sections join. The fiber need only loop around the flange once. Because of the diffusion of leaking gas, one loop will be in a position to intercept leaking gas from anywhere on the circumference. An electrical component 51 detects an electrical resistance of the sensor fiber 50. The resistance changes in the presence of certain chemical vapors. The design and manufacture of resistance detecting electrical components 51 is well known.

Figure 6:
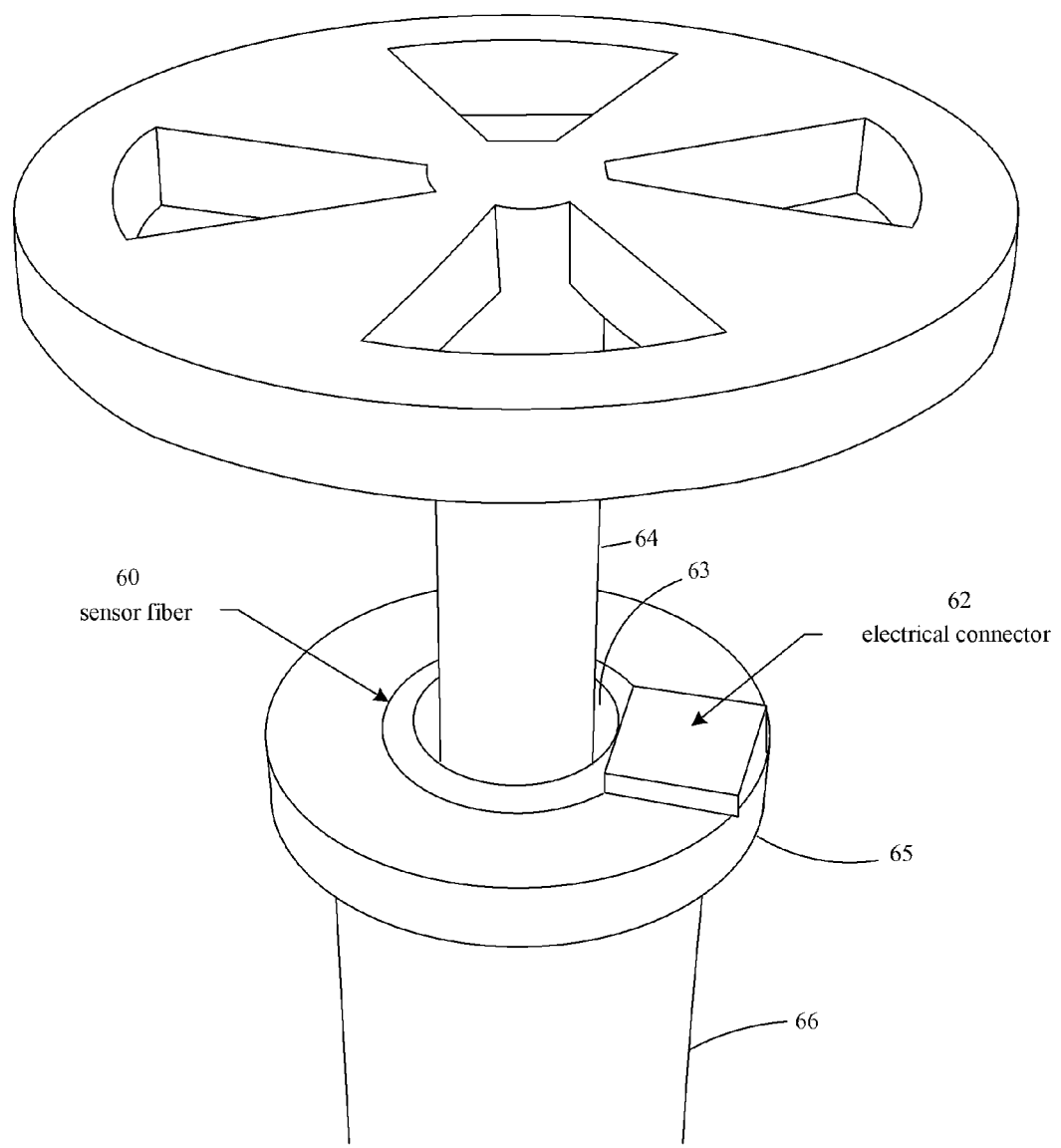
FIG. 6 illustrates a flange utilizing a fiber vapor sensor.

FIG. 6 illustrates the use of a fiber vapor sensor to detect gas leaks around the opening of a valve stem. A valve stem 64 protrudes into valve opening 63. Gas may potentially leak if a gasket, washer, or other component within the valve housing 66 becomes degraded or damaged. The sensor fiber 60 surrounds the valve opening 63 and an electrical component 62 measures the ongoing electrical resistance of the sensor fiber 60. As with a flange, the location of the fiber loop around the valve stem should be such that it is in a position to detect escaping gas from anywhere on the entire circumference. Resting the fiber loop on the top of the valve bushing will help ensure that the loop encounters escaping vapor from anywhere on the circumference of the stem. The component 62 may comprise two terminals for coupling with different ends of the fiber 60. The loop resistance is measured across the two terminals.

Figure 7:
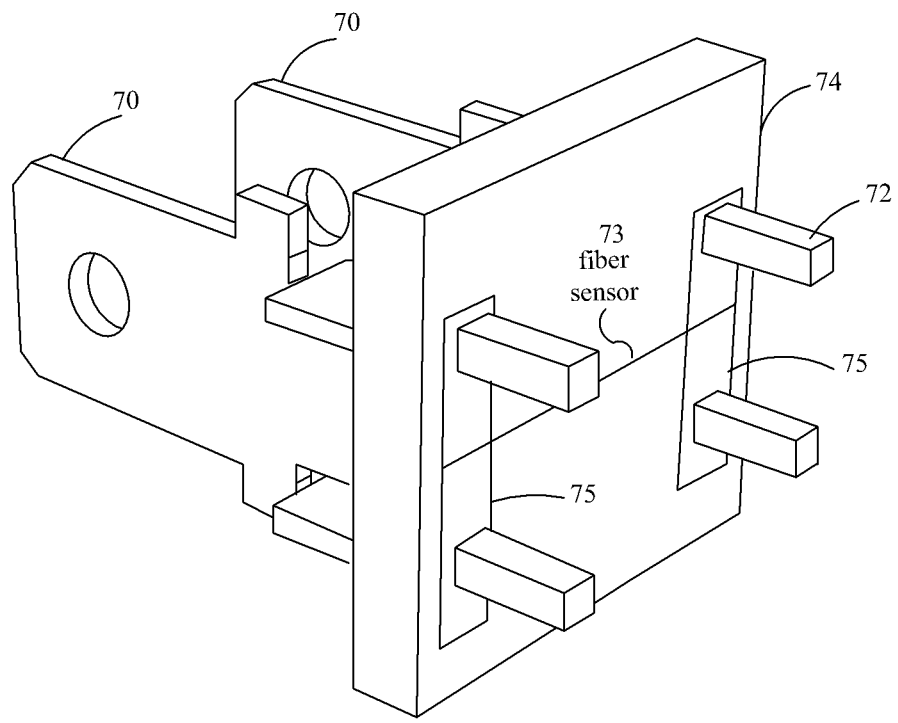
FIG. 7 illustrates a FVIR power vent water heater fiber vapor sensor.

FIG. 7 illustrates a FVIR (Flammable Vapor Ignition Resistant) power vent water heater fiber vapor sensor. The thread sensor 73 is painted down to a PCB (printed circuit board) 74 with conducting silver paint 75. The silver paint 75 connects the opposite ends of the thread sensor 73 to two quick connectors 72 soldered to the PCB 74. The quick connect terminals 70 are used to connect the sensor terminal block to a smart gas valve. The gas valves remain open, or close, depending on the output signal from the quick connect blocks.

What is claimed is:

1. A vapor sensor, comprising:
    a single glass filament less than 2 millimeters in diameter and greater than 1 millimeters in length, the filament having a first end and a second end separated by a long axis and comprising electrodes at each end;
    the filament coated with a resilient material; and
    a first layer of conducting particles embedded in the resilient material and forming a conducting path between ends of the filament.

2. The vapor sensor of claim 1, the first layer of conducting particles comprising:
    one of palladium, graphite, tungsten disulfide, silver, platinum, aluminum, gold, ruthenium, tantalum, iridium, or carbon.

3. The vapor sensor of claim 1, the first layer of conducting particles comprising:
    particles each having a radius that is greater than a tenth and less than ten times a radius of the filament.

4. The vapor sensor of claim 1, the resilient coating material for the fiber comprising:
    silicone.

5. The vapor sensor of claim 1, further comprising:
    a second layer of conductive particles coating the first layer of conducting particles, and adhering to the first layer of conducting particles without being chemically bonded to the first layer of conducting particles.

6. The vapor sensor of claim 5, the second layer of conductive particles further comprising:
    one of palladium, graphite, tungsten disulfide, silver, platinum, aluminum, gold, ruthenium, tantalum, iridium, or carbon;
    the particles of the second layer of conductive particles having an average radius the same order of magnitude as an average radius of particles of the first layer of conducting particles.

7. The vapor sensor of claim 5, further comprising:
    the first layer of conducting particles comprising ruthenium particles less than 100 microns in diameter, on average, and the second layer of particles comprising tungsten disulfide less than 10 microns in diameter, on average.

8. The vapor sensor of claim 1, further comprising:
    the particles of the first layer of particles having an average diameter less than 500 microns.

9. The vapor sensor of claim 1, the resilient stratum comprising:
    a siloaxane.

10. The vapor sensor of claim 1, further comprising:
    the filament is approximately 100 microns in diameter, and the first conductive particles are flake graphite.

11. A method of manufacturing a vapor sensor, comprising:
    drawing a non-conducting filament less than 2 millimeters in diameter;
    coating the filament with a resilient material;
    applying a first layer of conducting particles to the resilient material to form an electrically conducting path along the filament;
    curing the filament; and
    cutting the filament into a length not less than 1 millimeters, the length having a first end and a second end separated by a long axis.

12. The method of claim 11, the first layer of conducting particles comprising:
    one of palladium, graphite, tungsten disulfide, silver, platinum, platinum black, aluminum, gold, ruthenium, tantalum, rhenium, iridium, or carbon.

13. The method of claim 11, the first layer of conducting particles comprising:
    particles each having a radius that is greater than a tenth and less than twice a radius of the filament.

14. The method of claim 11, the resilient coating material for the fiber comprising:
    silicone.

15. The method of claim 11, further comprising:
coating the first layer of conductive particles with a second layer of conductive particles, and adhering the second layer to the first layer without chemical bonding.

16. The method of claim 15, the second layer of conductive particles further comprising:
one of palladium, graphite, tungsten disulfide, silver, platinum, platinum black, aluminum, gold, ruthenium, tantalum, rhenium, iridium, or carbon;
the particles of the second layer of conductive particles having an average radius approximately the same as an average radius of particles of the first layer of conducting particles.

17. The method of claim 15, further comprising:
the first layer of conducting particles comprising ruthenium particles less than 100 microns in diameter, on average, and the second layer of particles comprising tungsten disulfide less than 10 microns in diameter, on average.

18. The method of claim 11, further comprising:
the particles of the first layer of particles having an average diameter less than 500 microns.

19. The method of claim 11, the resilient stratum comprising:
a siloaxane.

20. The method of claim 11, further comprising:
the filament is approximately 100 microns in diameter, and the first conductive particles are flake graphite.

\* \* \* \* \*